United States Patent
Mikawa et al.

[11] 3,947,274
[45] Mar. 30, 1976

[54] SILVER HALIDE PHOTOGRAPHIC MATERIAL CONTAINING AN ISOUREA DERIVATIVE AS ANTIFOGGANT

[75] Inventors: Akikazu Mikawa; Ikutaro Horie; Keiichi Adachi; Hisashi Shiraishi, all of Minami-ashigara, Japan

[73] Assignee: Fuji Photo Film Co., Ltd., Minami-ashigara, Japan

[22] Filed: May 14, 1974

[21] Appl. No.: 469,924

[30] Foreign Application Priority Data
May 15, 1973 Japan................... 48-53905

[52] U.S. Cl. .............. 96/107; 96/109; 96/111; 96/120; 96/114.5
[51] Int. Cl.² ............................ G03C 1/34
[58] Field of Search ............ 96/107, 109, 66.5, 111, 96/120, 114.5

[56] References Cited
UNITED STATES PATENTS

| | | | |
|---|---|---|---|
| 2,363,493 | 11/1944 | Baldsiefen | 96/109 |
| 3,565,631 | 2/1971 | Oguchi et al. | 96/109 |
| 3,732,104 | 5/1973 | Vandenabeele et al. | 96/109 |
| 3,811,896 | 5/1914 | Herz et al. | 96/109 |

*Primary Examiner*—Won H. Louie, Jr.
*Attorney, Agent, or Firm*—Sughrue, Rothwell, Mion, Zinn & Macpeak

[57] ABSTRACT

A photographic light-sensitive material comprising a support having thereon at least one silver halide photographic emulsion layer with at least one of the layers of the photographic light-sensitive material containing a compound represented by the following general formula (I) or (II)

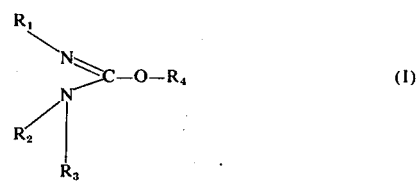

(I)

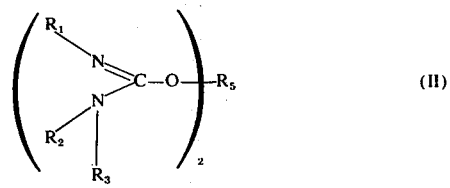

(II)

wherein $R_1$, $R_2$, and $R_3$ each represents a hydrogen atom, an alkyl group, an aryl group or a heterocyclic ring residue, and $R_2$ and $R_3$ can combine to form an alkylene group; $R_4$ represents those groups other than a hydrogen atom as described for $R_1$, $R_2$ and $R_3$; and $R_5$ represents an alkylene group of a polyoxyalkylene group having at least 4 carbon atoms, or the organic acid salt or mineral acid salt thereof.

11 Claims, No Drawings

SILVER HALIDE PHOTOGRAPHIC MATERIAL CONTAINING AN ISOUREA DERIVATIVE AS ANTIFOGGANT

BACKGROUND OF THE INVENTION

1. Field of the Invention

The present invention relates to a silver halide light-sensitive material and, more particularly, it relates to a light-sensitive material in which fog occurs to a lesser extent.

2. Description of the Prior Art

As a method for rapidly processing light-sensitive materials, it is known to develop at an elevated temperature. In recent years, this method has been applied to the processing of various light-sensitive materials with some success. However, in general, development of light-sensitive materials at an elevated temperature tends to cause fog, which deteriorates the photographic quality. (The term "elevated temperature" as used herein means a temperature of at least about 30°C up to about 45°C.) In particular, when a developer containing a hardening substance (e.g., glutaraldehyde, etc.), such as a commercially available developer for rapidly processing X-ray films, is used, films sometimes are seriously fogged by the developer, especially when the developer is exhausted or fatigued (i.e., when the amount of films processed approaches almost the limit of the processing capability of the developer).

In general, the photographic sensitivity of a silver halide photographic emulsion is enhanced by a sulfur compound, a reducing agent, a noble metal or a polyalkylene oxide compound. However, these sensitizing methods increase the fogging tendency as well as the photographic sensitivity. Therefore, various anti-fogging agents are added to photographic emulsions.

Typical examples of anti-fogging agents are 4-hydroxy-6-methyl-1,3,3a,7-tetrazaindene and 1-phenyl-5-mercaptotetrazole. The former compound markedly suppresses the increase of fogging of light-sensitive materials or photographic emulsions during storage. However, this compound exhibits only a small anti-fogging effect in controlling fog immediately after the production of the light-sensitive material. On the other hand, the latter compound controls fog immediately after production. Therefore, favorable results are obtained by using these two compounds in combination.

However, when light-sensitive materials are processed at an elevated temperature, 4-hydroxy-6-methyl-1,3,3a,7-tetrazaindene does not exhibit a marked fog controlling effect, while 1-phenyl-5-mercaptotetrazole, when used in a sufficient amount to control fog, deteriorates the sensitivity so seriously that the use of this compound is not practical.

Thus, in elevated temperature development, it has been difficult to control fogging sufficiently using the aforesaid anti-fogging agents to the same extent as in ordinary development (e.g., conducted at about 20°C).

SUMMARY OF THE INVENTION

It is, therefore, an object of the present invention to provide a light-sensitive material which can be developed at an elevated temperature with less fog and less reduction in sensitivity.

As a result of various investigations, it has been found that a light-sensitive material which contains in a photographic layer and/or other hydrophilic colloid layer or layers (e.g., an interlayer, a protective layer, etc.) at least one compound represented by the following formulae

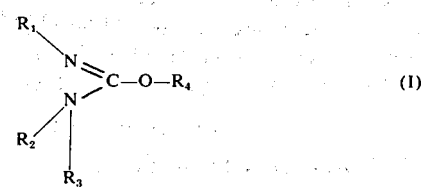

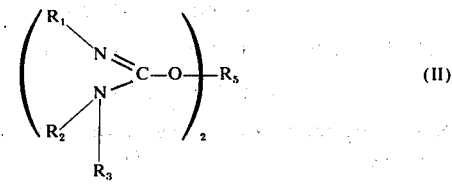

wherein $R_1$, $R_2$, and $R_3$ each represents a hydrogen atom, an alkyl group, an aryl group or a heterocyclic ring residue, and $R_2$ and $R_3$ may combine to form an alkylene group forming a ring; $R_4$ represents those groups other than a hydrogen atom as described for $R_1$, $R_2$ and $R_3$; and $R_5$ represents an alkylene group or a polyoxyalkylene group having at least 4 carbon atoms; or an organic acid salt or a mineral acid salt thereof (including inner salts) exhibits outstanding fog-controlling effects when processed at an elevated temperature with less reduction, if any, in sensitivity even if scarcely any anti-fogging effects are exhibited when processed at temperatures used in ordinary development (at about 20°C). This phenomenon due to the addition of these compounds is not expected at all from conventional knowledge and is really a surprising discovery.

DETAILED DESCRIPTION OF THE INVENTION

In the above-illustrated formulae, $R_1$, $R_2$, and $R_3$ each represents a hydrogen atom, an alkyl group [preferably an alkyl group whose alkyl moiety contains 12 or less, more preferably 1 to 6, carbon atoms; for example, methyl, ethyl, propyl, butyl, etc.; a cycloalkyl group (e.g., a cyclohexyl group, etc.); a substituted alkyl group {such as an aralkyl group (e.g., a benzyl group, etc.), an alkoxyalkyl group (e.g., an ethoxyethyl group, etc.), an N,N-dialkylaminoalkyl group (e.g., an N,N-dimethylaminoethyl group, etc.), a hydroxysulfonyloxyalkyl group (e.g., a hydroxysulfonyloxypropyl group, etc.), a vinylmethyl group, an aryloxyalkyl group (e.g., a phenoxyethyl group, etc.), a furnylalkyl group (e.g., a furanylmethyl group, etc.), a sulfoalkyl group (e.g., a sulfopropyl group, etc.), etc.} and the like]; an aryl group { such as a phenyl group, a tolyl group, an anisyl group, an N,N-dialkylaryl group (e.g., an N,N-dimethylanil group, etc.), and the like}; a heterocyclic group {such as a nitrogen-containing 6-membered ring group (e.g., a pyridyl group, a 2,2,6,6-tetramethyl-4-piperidyl group, etc.), etc.}; $R_2$ and $R_3$ may combine as an alkylene group to form a ring (such as a 5-membered ring); $R_4$ represents those groups other than a hydrogen atom set forth for $R_1$, $R_2$ and $R_3$; and $R_5$ represents an alkylene group or a polyoxyalkylene group having at least 4 up to about 8 carbon atoms.

As salts of organic acids, either the salts of carboxylic acids or aromatic sulfonic acids can be satisfactorily used. Specific examples thereof include the salts of p-toluenesulfonic acid, oxalic acid, and the like.

COMPOUND 1

N,N'-Dicyclohexyl-O-methylisourea

COMPOUND 2

N,N'-Dicyclohexyl-O-methylisouronium oxalate

COMPOUND 3

N,N'-Dicyclohexyl-O-methylisouronium p-toluenesulfonate

COMPOUND 4

N,N'-Dicyclohexyl-O-ethylisourea

COMPOUND 5

N,N'-Dicyclohexyl-O-ethylisouronium oxalate

COMPOUND 6

N,N'-Dicyclohexyl-O-ethylisouronium p-toluenesulfonate

COMPOUND 7

N,N'-Dicyclohexyl-O-n-butylisourea

COMPOUND 8

N,N'-Dicyclohexyl-O-n-butylisouronium oxalate

COMPOUND 9

N,N'-Diethyl-O-cyclohexylisourea

COMPOUND 10

N,N'-Diethyl-O-cyclohexylisouronium oxalate

COMPOUND 11

N,N'-Dicyclohexyl-O-phenylisouronium oxalate

COMPOUND 12

N,N'-Diphenyl-O-ethylisourea

COMPOUND 13

N,N'-Diisopropyl-O-methylisourea

COMPOUND 14

N,N'-Diisopropyl-O-methylisouronium oxalate

COMPOUND 15

N,N'-Diisopropyl-O-ethylisourea

COMPOUND 16

N,N'-Diisopropyl-O-(2-ethoxyethyl)isourea

COMPOUND 17

N,N'-Diisopropyl-O-(2-N,N-diethylaminoethyl)isourea

COMPOUND 18

N,N'-Diisopropyl-O-isopropylisourea

COMPOUND 19

N,N'-Diisopropyl-O-isopropylisouronium oxalate

COMPOUND 20

N,N'-Diisopropyl-O-t-butylisourea

COMPOUND 21

N,N-Diisopropyl-O-(2-phenoxyethyl)isourea

COMPOUND 22

N,N'-Diisopropyl-O-n-octylisourea

COMPOUND 23

N,N'-Di-n-butyl-O-cyclohexylisourea

COMPOUND 24

N-Methyl-N'-t-butyl-O-methylisourea

COMPOUND 25

N-Methyl-N'-t-butyl-O-ethylisourea

COMPOUND 26

N,N'-Diisopropyl-O-benzylisourea

COMPOUND 27

N,N'-Diisopropyl-O-furfurylisourea

COMPOUND 28

N,N'-Di-n-butyl-O-n-butylisourea

COMPOUND 29

N-n-Butyl-N'-cyclohexyl-O-methylisourea

COMPOUND 30

O,O'-Tetramethylene-bis(N,N'-diisopropylisourea)

COMPOUND 31

O,O'-Hexamethylene-bis(N,N'-diisopropylisourea)

COMPOUND 32

N,N'-Diethyl-O-(3-hydroxysulfonyloxypropyl)isourea

COMPOUND 33

O-(3-Hydroxysulfonyloxypropyl)isourea

COMPOUND 34

N,N'-Dimethyl-O-(3-hydroxysulfonyloxypropyl)isourea

COMPOUND 35

O,O'-Tetramethylene-bis(N,N'-dicyclohexylisourea)

COMPOUND 36

N,N'-Diisopropyl-O-allylisourea

COMPOUND 37

N,N-Tetramethylene-O-dodecylisourea

COMPOUND 38

N,N'-Di(4-pyridyl)-O-ethylisourea

The compounds of the above-illustrated formulae can be synthesized by reacting a carbodiimide with an alcohol in the presence of cuprous chloride as disclosed in E. Schmidt and F. Mosmuller, *Ann.*, 597, 235 (1955) or in the presence of zinc chloride. The salts thereof can be readily obtained by mixing the compounds with an acid using a suitable solvent. Also, by reacting an appropriate urea with a sultone as disclosed in K. Furukawa, I. Tamai and R. Oda; *Journal of Industrial*

*Chemistry*, 59, 1028 (1956), inner salts can be formed. Examples of the synthesis of compounds included in the above-illustrated general formulae, which are suitable for use in the present invention, are given below. Unless otherwise indicated herein, all parts, percents, ratios and the like are by weight.

SYNTHESIS EXAMPLE 1 (COMPOUND 1)

25 grams of N,N'-dicyclohexylcarbodiimide, 3.7 g of methanol and a catalytic amount of zinc chloride were mixed and heated for 2 hours over a water bath. Then, the resulting oily product was distilled under reduced pressure. b.p.130°–132°C/2 mmHg; yield: 27.6 g (95%). Alternatively, a catalytic amount of cuprous chloride or cupric chloride can be substituted for the zinc chloride employed in this example.

SYNTHESIS EXAMPLE 2 (COMPOUND 2)

10 grams of N,N'-dicyclohexylisourea, obtained in Synthesis Example 1, was dissolved in 50 ml of dry acetone. Upon adding dropwise thereto, under stirring, 4.5 g of oxalic acid dissolved in 50 ml of acetone, crystals precipitated. After recrystallization of the crude product from ethanol, 13.5 g of needle-like crystals, m.p.201°–203°C, were obtained.

SYNTHESIS EXAMPLE 3 (COMPOUND 3)

10 grams of N,N'-dicyclohexylisourea, obtained in Synthesis Example 1, was dissolved in 50 ml of dry acetone. Upon adding dropwise thereto, under cooling and stirring, 8.5 g of p-toluene-sulfonic acid dissolved in 50 ml of acetone, crystals precipitated. The crude product was recrystallized from acetone to obtain 16.5 g of colorless, needle-like crystals, m.p.144°–145°C.

SYNTHESIS EXAMPLE 4 (COMPOUND 22)

11.6 grams of diethylurea and 12.2 g of propanesultone were mixed and gradually heated with stirring. When the internal temperature reached 50°–60°C, the contents became uniform and the reaction took place rapidly. Upon recrystallization of the crude product from acetone, 20 g of crystals having a melting point of 156°–157°C were obtained.

The compounds which can be used in the present invention can be added to silver halide emulsions, during chemical ripening or, preferably, after chemical ripening, by dissolving them in water, methanol or a similar water-miscible solvent. The compounds are added in a sufficient quantity to effectively prevent fog. This amount can suitably be determined by those skilled in the art depending upon the degree of ripening, kind of emulsion and the like. Generally, a suitable amount ranges from about 0.01 g to 50 g, preferably 0.5 to 5 g, per 1 mol of silver halide.

Silver halide emulsions are usually prepared by mixing a solution of a water-soluble silver salt (e.g., silver nitrate, etc.) with a solution of a water-soluble halide (e.g., potassium bromide, etc.) in the presence of a solution of a water-soluble high polymer such as gelatin. Particularly favorable results are obtained using silver bromoiodide and silver chlorobromoiodide as the silver halide A more preferable silver halide is silver bromoiodide or silver chlorobromoiodide containing about 1 mol% to about 8 mol% silver iodide.

The grains of the silver halide can be in a cubic form, octahedral form, a mixed form thereof, etc.

These silver halide grains can be prepared according to conventional methods. For example, a single or double jet method, a controlled double jet, or the like, can be employed.

Also, two or more silver halide emulsions which have been prepared separately can be mixed with each other. Furthermore, with respect to the crystal structure of the silver halide grains, those grains in which the crystal structure is uniform, those grains in which the inner portion and the outer portion form a different stratum structure, or those grains of the so-called converted type as described in British patent No. 635,841 and U.S. Pat. No. 3,622,318 can all be suitably employed. Those emulsions in which latent images are mainly formed on the surface of the grains or those in which latent images are formed inside the grains (internal latent image type) are usable. These photographic emulsions are well-known in the art, for example, as described in Mees and James, *The Theory of the Photographic Process*, MacMillan Co. and Grafikides; *Photographic Chemistry*, Fauntain Press, and can be prepared according to various processes including using an ammoniacal process, a neutral process, an acidic process, etc.

These silver halide grains can be washed after formation so as to remove water-soluble salts produced as a by-product (e.g., potassium nitrate in the case of producing silver bromide using silver nitrate and potassium bromide) from the system and heat-processing them in the presence of a chemical sensitizer to enhance the sensitivity without making the grains coarse.

Suitable hydrophilic collids which can be used (as a vehicle), are proteins such as gelatin, colloidal albumin, casein, etc.; cellulose derivativs such as carboxymethyl cellulose, hydroxyethyl cellulose, etc.; polysaccharides such as agar-agar, sodium alginate, starch derivatives, etc.; synthetic hydrophilic colloids such as polyvinyl alcohol, poly-N-vinylpyrrolidone, polyacrylic acid copolymers, polyacrylamide and derivatives thereof, etc. If desired, a compatible mixture of two or more of these colloids can be used. Of these, gelatin is the most commonly used. Part or all of the gelatin can be replaced by a synthetic high polymer substance, by a gelatin derivative prepared by processing gelatin with a reagent having a group capable of reacting with the functional groups in the gelatin molecules (i.e., amino groups, imino groups, hydroxy groups and carboxy groups), or by a graft polymer prepared by connecting or grafting the molecular chain of other high polymer substances with gelatin.

Appropriate reagents which can be used to prepare the above-described gelatin derivatives are the isocyanates as described in U.S. Pat. No. 2,614,928, the acid chlorides, acid anhydrides, acid anhydrides described in U.S. Pat. No. 3,118,766, the bromoacetic acids as described in Japanese Pat. publication No. 5514/64, the phenyl glycidyl ethers as described in Japanese Pat. publication No. 21845/67, the vinylsulfone compounds described in U.S. Pat. No. 3,132,945, N-allylvinylsulfonamides described in British patent No. 861,414, the maleinimides as described in U.S. Pat. No. 3,186,846, the acrylonitriles as described in U.S. Pat. No. 2,594,293, the polyalkyleneoxides described in U.S. Pat. No. 3,312,553, the epoxy compounds described in Japanese Pat. publication No. 26845/67, the acid esters as described in U.S. Pat. No. 2,763,639, and the alkanesultones as described in British patent No. 1,033,189.

Many descriptions of high polymers which can be grafted to gelatin, are set forth in U.S. Pat. Nos.

2,763,625, 2,831,767, 2,956,884, *Polymer Letters*, 5, 595 (1967), *Photo. Sci. Eng.*, 9, 148 (1965), *J. Polymer Sci.* A-1, 9, 3199 (1971), etc. In general, polymers or copolymers of monomers, the so-called vinyl monomers, such as acrylic acid, methacrylic acid, or the ester, amide or nitrile derivatives thereof, styrene, and the like are widely used. Of these, however, hydrophilic vinyl polymers having some compatibility with gelatin, such as the polymers or copolymers of acrylic acid, acrylamide, methacrylamide, hydroxyalkyl acrylate, hydroxyalkyl methacrylate, etc. are particularly desirable.

The compounds of the present invention are not affected by the copresence of photographic additives conventionally used such as stabilizing agents such as 1-phenyl-5-mercaptotetrazole, 5-methylbenzotriazole, α-lipoic acid, etc., hardening agents, coating aids such as saponin, nonylphenyl ether of polyethylene oxide, etc., spectrally sensitizing agents such as a the cyanine dyes and merocyanine dyes as are described in C. E. K. Mees and T. H. James, *The Theory of Photographic Process*, pages 202–221 (1966), etc.

The hardening of emulsions can be effected using conventional techniques. Examples of hardeners include, e.g., formaldehyde, aldehyde compounds as described in U.S. Pat. No. 3,232,764, ketone compounds such as diacetyl, cyclopentanedione, etc.; compounds having a reactive halogen such as bis(2-chloroethylurea), 2-hydroxy-4,6-dichloro-1,3,5-triazine, and those described in U.S. Pat. Nos. 3,288,775, 2,732,303, British patent Nos. 974,723, 1,167,207, etc.; compounds having a reactive olefin group such as divinylsulfone, 5-acetyl-1,3-diacryloylhexahydro-1,3,5-triazine, and those described in U.S. Pat. Nos. 3,635,718, 3,232,763, British Pat. No. 994,869, etc.; N-methylol compounds such as N-hydroxymethylphthalimide and those described in U.S. Pat. Nos. 2,732,316, 2,586,168, etc.; isocyanates as described in U.S. Pat. No. 3,103,437; aziridine compounds as described in U.S. Pat. Nos. 3,017,280 and 2,983,611; acid derivatives as described in U.S. Pat. Nos. 2,725,294 and 2,725,295; carbodiimide compounds as described in U.S. Pat. No. 3,100,704; epoxy compounds as described in U.S. Pat. No. 3,091,537; isoxazole compounds as described in U.S. Pat. Nos. 3,321,313, and 3,543,292; halocarboxyaldehydes such as mucochloric acid, etc.; dioxane derivatives such as dihydroxydioxane, dichlorodioxane, etc.; inorganic hardening agents such as chromium alum, zirconium sulfate, etc.

Also, precursors of the above-described compounds such as an alkali metal bisulfite-aldehyde adduct, hydantoin methylol derivatives, primary aliphatic nitro alcohols, etc. can be used in place of the above-described compounds.

To the silver halide emulsion used in the present invention can be applied conventionally employed chemical sensitization methods such as gold sensitization (e.g., as described in U.S. Pat. Nos. 2,540,085, 2,597,856, 2,597,915, 2,399,083, etc.), sensitization with Group VIII metal ions, sulfur sensitization (e.g., as disclosed in U.S. Pat. Nos. 1,574,944, 2,278,947, 2,440,206, 2,410,689, 3,189,458, 3,415,649, etc.), reduction sensitization (e.g., as disclosed in U.S. Pat. Nos. 2,518,698, 2,419,974, 2,983,610, etc.), or a combination of these methods.

Specific examples of chemical sensitizing agents are sulfur sensitizing agents such as allylthiocarbamide, thiourea, sodium thiosulfate, cystine, etc.; noble metal sensitizing agents such as potassium chloroaurate, aurous thiosulfate, potassium chloropalladate, etc.; reduction sensitizers such as tin chloride, phenylhydrazine, reductone, etc. Also, the emulsion can contain sensitizers such as polyoxyethylene derivatives, polyoxypropylene derivatives, derivatives having a quaternary ammonium group, etc., plasticizers for dimensional stability, latex polymers, and matting agents.

Furthermore, an antifogging agent such as nitrobenzimidazole, ammonium chloroplatinate, etc., a stabilizer such as 4-hydroxy-6-methyl-1,3,3a,7-tetrazaindene, etc. can be incorporated in the emulsion. A coating aid such as saponin or sodium alkylbenzenesulfonate can also be present in the emulsion.

The photographic emulsion can be applied to a support. A suitable coating amount can range from about 10 to 200 mg, preferably 50 to 200 mg, as silver halide/100 $cm^2$ of the support. Although this coating amount can vary depending on the end-use purpose, the kind of silver halide, the presence of photographic additives. Typical flexible supports are those which are commonly used for photographic light-sensitive materials, such as cellulose nitrate films, cellulose acetate films, cellulose acetate butyrate films, cellulose acetate propionate films, polystyrene films, polyethylene terephthalate films, polycarbonate films, laminates thereof, thin glass films, and the like.

As the support, a transparent or opaque support can be selected depending upon the end-use purpose of the light-sensitive material. Also, in selecting a transparent support, colored transparent supports containing a dye or a pigment can be used as well as a colorless, transparent supports. This has so far been conducted in X-ray films, etc. and is described in the literature such as *J. SMPTE*, 67, 296 (1958), etc. Opaque supports include those which do not completely intercept light such as ordinary papers, plastic films containing titanium dioxide or a like white filler or films surface-processed according to a method as described in Japanese Pat. publication No. 19068/72, and supports which completely intercept light such as papers and plastics containing carbon black, a dye, etc.

Where the adhesivity between the support and the photographic emulsion layer is insufficient, a subbing layer can be provided on either of them. Also, in order to further improve the adhesiveness, the surface of the support can be subjected to a preliminary processing such as corona discharge, ultraviolet light-irradiation, flame treatment, etc. The present invention is preferably applied to an emulsion for X-ray films.

The developer used for the rapid processing at an elevated temperature preferably contains a hardener, e.g., glutaraldehyde, succinic aldehyde, etc. Rapid processing at an elevated temperature is well-known in the art and is described in, e.g., U.S. Pat. No. 3,677,761.

The present invention will now be illustrated in greater detail by reference to the following non-limiting examples of preferred embodiments of the present invention.

EXAMPLE 1

10 cc of a 1% solution of 4-hydroxy-6-methyl-1,3,3a,7-tetrazaindene was added to 1 kg of a gelatino-silver bromoiodide emulsion containing 1.5 mol% silver iodide and having been subjected to sulfur sensitization and gold sensitization. Then, 30 cc of 10% saponin and 20 cc of 1% mucochloric acid were added thereto. The resulting emulsion was separated into 6 equal portions. One portion was used as a control. To the remaining portions were added, respectively, a compound as set forth in Table 1. Each of the resulting emulsion portions was coated on a polyester base in a silver amount of 50 mg/100 cm² and dried to prepare samples. The thus prepared samples were exposed using a NSG II-type sensitometer and developed using the following developers. The results given in Table 1 were obtained.

| Developer (I) | |
|---|---|
| 1-Phenyl-3-pyrazolidone | 0.5 g |
| Sodium Sulfite (anhydrous) | 70 g |
| Hydroquinone | 9 g |
| Sodium Carbonate (monohydrate) | 35 g |
| Sodium Bromide | 5 g |
| Water to make | 1 liter |
| Developer (II) | |
| Sodium Sulfite | 40 g |
| Hydroquinone | 25 g |
| Boric Acid | 10 g |
| 1-Phenyl-3-pyrazolidone | 1.5 g |
| Potassium Hydroxide | 30 g |
| 5-Methylbenzotriazole | 0.15 g |
| Glutaraldehyde Bisulfite | 15 g |
| Acetic Acid | 12 g |
| Potassium Bromide | 10 g |
| Water to make | 1 liter |

Table 1

| | Amount Added g/mol Ag | Developer (I) 20°C, 4 min. | | Developer (II) 35°C, 30 sec. | |
|---|---|---|---|---|---|
| | | Fog | Specific Sensitivity | Fog | Specific Sensitivity |
| Control | — | 0.04 | 100 (standard) | 0.16 | 80 |
| Compound (1) | 2.0 | 0.04 | 100 | 0.04 | 64 |
| Compound (2) | 2.0 | 0.04 | 95 | 0.05 | 72 |
| Compound (4) | 2.0 | 0.04 | 100 | 0.04 | 68 |
| Compound (6) | 2.0 | 0.04 | 95 | 0.05 | 74 |
| 1-Phenyl-5-mercapto-tetrazole (comparative compound) | 0.027 | 0.02 | 58 | 0.12 | 42 |

The above results clearly demonstrate that a silver halide emulsion containing the additive of the present invention is fogged less in the development at an elevated temperature using Developer (II) and undergoes an extremely small reduction in sensitivity in development using Developer (I).

EXAMPLE 2

10 cc of a 1% solution of 4-hydroxy-6-methyl-1,3,3a,7-tetrazaindene was added to 1 kg of a silver bromoiodide emulsion containing 5 mol% silver iodide and having been subjected to sulfur sensitization and gold sensitization. Then, 30 cc of 10% saponin and 20 cc of 1% mucochloric acid were added thereto. The resulting emulsion was separated into 5 equal portions. One portion was used as a control. To each of the remaining portions was added a compound as set forth in Table II. Each of the resulting emulsion portions was coated on a polyester base in a silver amount of 60 mg/100 cm² and dried to prepare samples. The thus prepared samples were exposed using an NSG II type sensitometer and developed in the same two developers as described in Example 1. Thus, the results given in Table II were obtained.

Table II

| | Amount Added g/mol AgX | Developer (I) 20°C, 4 min. | | Developer (III) 40°C, 30 sec. | |
|---|---|---|---|---|---|
| | | Fog | Sensitivity | Fog | Sensitivity |
| Control | — | 0.04 | 100 (standard) | 0.32 | 115 |
| Compound (9) | 2.0 | 0.04 | 100 | 0.08 | 104 |
| Compound (11) | 2.0 | 0.04 | 95 | 0.04 | 88 |
| Compound (14) | 2.0 | 0.04 | 95 | 0.07 | 98 |
| Compound (11) plus Compound (14) | 1.0 1.0 | 0.04 | 95 | 0.05 | 93 |

The above results clearly show that the silver halide emulsion containing the additive of the present invention fogs less in the development at an elevated temperature using Developer (II) and undergoes a much smaller reduction in sensitivity in development using Developer (I).

EXAMPLE 3

A silver chlorobromoiodide emulsion comprising 1.5 mol% silver iodide, 0.5 mol% silver chloride and 98 mol% silver bromide was subjected to gold sensitization and sulfur sensitization, and, after adding thereto the same photographic additives as described in Example 1, the emulsion was separated into 10 equal portions. One portion was used as a control. To each of the remaining portions was added a compound shown in Table III and the portions were coated on a polyethylene terephthalate base and then dried. These thus prepared samples were exposed and developed at 40°C for 30 seconds in the same Developer II as described in Example 1 to obtain the results given in Table III.

Table III

| | Amount added g/mol AgX | | Specific Sensitivity |
|---|---|---|---|
| Control | — | 0.36 | 100 (standard) |
| Compound (26) | 0.5 | 0.19 | 121 |
| | 2 | 0.05 | 100 |
| | 8 | 0.05 | 98 |
| Compound (32) | 0.05 | 0.24 | 110 |
| | 2 | 0.08 | 102 |
| | 8 | 0.05 | 98 |
| Compound (35) | 0.05 | 0.11 | 105 |
| | 2 | 0.06 | 98 |
| | 8 | 0.05 | 98 |

From the above results, it can be seen that the silver halide emulsion containing the compound of the present invention shows a remarkable anti-fogging action when developed in Developer (II) at an elevated temperature.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive material comprising a support having thereon at least one silver halide photographic emulsion layer, with at least one of the layers of said photographic light-sensitive material containing a compound represented by the following general formula (I) or (II)

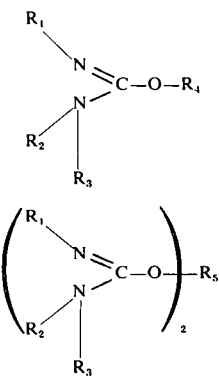

wherein $R_1$, $R_2$, and $R_3$ each represents a hydrogen atom, an alkyl group, an aryl group or a 6-membered heterocyclic ring group containing 1 nitrogen atom, and $R_2$ and $R_3$ can combine to form an alkylene group so that a 5-membered ring may be formed; $R_4$ represents those groups other than a hydrogen atom as described for $R_1$, $R_2$ and $R_3$; and $R_5$ represents an alkylene group or a polyoxyalkylene group having at least 4 carbon atoms or the organic acid salt or mineral acid salt thereof; said compound being employed in an amount from about 0.01g to 50g per 1 mol of silver halide.

2. The photographic light-sensitive material of claim 1, wherein said alkyl group is an unsubstituted alkyl group, a cycloalkyl group, or a substituted alkyl group substituted with a substituent selected from the group consisting of an aryl group, an alkoxy group, an N,N-dialkylamino group, a hydroxysulfonyloxy group, a vinyl group, an aryloxy group, a furyl group, and a sulfo group.

3. The photographic light-sensitive material of claim 1, wherein said silver halide is silver bromoiodide or silver chlorobromoiodide.

4. The photograhic light-sensitive material of claim 3, wherein said silver bromoiodide and silver chlorobromoiodide contains from about 1 to about 8 mol% silver iodide.

5. The photographic light-sensitive material of claim 1, wherein said photographic light-sensitive material contains at least one of a stabilizing agent, a hardening agent, a spectral sensitizing agent and a coating aid.

6. The photographic light-sensitive material of claim 1, wherein said silver halide emulsion is chemically sensitized.

7. The photographic light-sensitive material of claim 1, wherein said compound represented by the general formulae (I) is N,N'-dicyclohexyl-O-methylisouronium oxalate.

8. The photographic light-sensitive material of claim 1, wherein said compound represented by the general formulae (I) is N,N'-dicyclohexyl-O-methylisouronium p-toluenesulfonate.

9. The photographic light-sensitive material of claim 1, wherein said compound represented by the general formulae (I) is N,N'-dicyclohexyl-O-ethylisouronium oxalate.

10. The photographic light-sensitive material of claim 1, wherein said compound represented by the general formulae (I) is N,N'-dicyclohexyl-O-ethylisouronium p-toluenesulfonate.

11. The photographic light-sensitive material of claim 1, wherein said compound represented by the general formulae (I) is N,N'-dicyclohexyl-O-n-butylisouronium oxalate.

* * * * *